(12) United States Patent
Jiang et al.

(10) Patent No.: US 10,995,367 B2
(45) Date of Patent: *May 4, 2021

(54) VESICULAR ADAPTOR AND USES THEREOF IN NUCLEIC ACID LIBRARY CONSTRUCTION AND SEQUENCING

(71) Applicant: MGI TECH CO., LTD., Shenzhen (CN)

(72) Inventors: Yuan Jiang, Shenzhen (CN); Jing Guo, Shenzhen (CN); Xiaojun Ji, Shenzhen (CN); Chunyu Geng, Shenzhen (CN); Kai Tian, Shenzhen (CN); Xia Zhao, Shenzhen (CN); Huaiqian Xu, Shenzhen (CN); Wenwei Zhang, Shenzhen (CN); Hui Jiang, Shenzhen (CN); Radoje Drmanac, Los Altos Hill, CA (US)

(73) Assignee: MGI TECH CO., LTD., Shenzhen (CN)

( * ) Notice: Subject to any disclaimer, the term of this patent is extended or adjusted under 35 U.S.C. 154(b) by 74 days.

This patent is subject to a terminal disclaimer.

(21) Appl. No.: 16/576,582

(22) Filed: Sep. 19, 2019

(65) Prior Publication Data

US 2020/0080140 A1 Mar. 12, 2020

Related U.S. Application Data (63) Continuation of application No. 15/510,890, filed as application No. PCT/CN2014/091852 on Nov. 21, 2014, now Pat. No. 10,544,451, which is a continuation-in-part of application No. PCT/CN2014/086418, filed on Sep. 12, 2014.

(51) Int. Cl.
| | | |
|---|---|---|
| *C12Q 1/6853* | (2018.01) | |
| *C12N 15/66* | (2006.01) | |
| *C12Q 1/6806* | (2018.01) | |
| *C40B 40/08* | (2006.01) | |
| *C40B 50/06* | (2006.01) | |
| *B01J 19/00* | (2006.01) | |
| *C12N 15/10* | (2006.01) | |
| *C12Q 1/6811* | (2018.01) | |
| *C12Q 1/6837* | (2018.01) | |
| *C12Q 1/686* | (2018.01) | |
| *C40B 60/14* | (2006.01) | |
| *C12Q 1/6855* | (2018.01) | |
| *C12Q 1/6874* | (2018.01) | |
| *C12N 9/22* | (2006.01) | |
| *C12N 9/00* | (2006.01) | |
| *C12N 11/06* | (2006.01) | |
| *C40B 50/14* | (2006.01) | |

(52) U.S. Cl.
CPC ........ *C12Q 1/6853* (2013.01); *B01J 19/0046* (2013.01); *C12N 9/22* (2013.01); *C12N 9/93* (2013.01); *C12N 11/06* (2013.01); *C12N 15/10* (2013.01); *C12N 15/1065* (2013.01); *C12N 15/1082* (2013.01); *C12N 15/1093* (2013.01); *C12N 15/66* (2013.01); *C12Q 1/6806* (2013.01); *C12Q 1/686* (2013.01); *C12Q 1/6811* (2013.01); *C12Q 1/6837* (2013.01); *C12Q 1/6855* (2013.01); *C12Q 1/6874* (2013.01); *C40B 40/08* (2013.01); *C40B 50/06* (2013.01); *C40B 50/14* (2013.01); *C40B 60/14* (2013.01); *B01J 2219/00529* (2013.01); *C12Q 2525/191* (2013.01); *C12Q 2565/537* (2013.01)

(58) Field of Classification Search
CPC .................................................... C12Q 1/6853
USPC .......................................................... 506/16
See application file for complete search history.

(56) References Cited

U.S. PATENT DOCUMENTS

| | | |
|---|---|---|
| 2007/0172839 A1 | 7/2007 | Smith et al. |
| 2010/0069263 A1 | 3/2010 | Shendure et al. |
| 2012/0122161 A1 | 5/2012 | Musgrave-Brown et al. |

FOREIGN PATENT DOCUMENTS

| | | |
|---|---|---|
| CN | 102181943 A | 9/2011 |
| CN | 102296065 A | 12/2011 |
| CN | 103014137 A | 4/2013 |
| CN | 103103624 A | 5/2013 |
| WO | 01/40516 A2 | 6/2001 |
| WO | 2007076420 A2 | 7/2007 |
| WO | 2007/087291 A2 | 8/2007 |
| WO | 2007087291 A2 | 8/2007 |
| WO | 2007140417 A2 | 12/2007 |
| WO | 2008070375 A2 | 12/2007 |
| WO | 2008070352 A2 | 6/2008 |
| WO | 2009/061840 A1 | 5/2009 |
| WO | 2009/133466 A2 | 11/2009 |
| WO | 2012037876 A1 | 3/2012 |
| WO | 2012037880 A1 | 3/2012 |
| WO | 2012079486 A1 | 6/2012 |
| WO | 2012162267 A2 | 11/2012 |

(Continued)

OTHER PUBLICATIONS

Office Action dated Nov. 13, 2018 for CN application 201480081687. 4.

(Continued)

*Primary Examiner* — Karla A Dines
(74) *Attorney, Agent, or Firm* — Westman, Champlin & Koehler, P.A.; Z. Peter Sawicki; Amanda M. Prose (57) ABSTRACT

Provided are a vesicular adaptor and a single-chain cyclic library constructed by using the adaptor. The library can be used for RNA sequencing and other sequencing platforms dependent on a single-stranded cyclic library, and has the advantage of high throughput sequencing, high accuracy and simple operations.

19 Claims, 2 Drawing Sheets

Specification includes a Sequence Listing.

(56) References Cited

FOREIGN PATENT DOCUMENTS

| WO | 2016/078095 A1 | 5/2016 |
|---|---|---|
| WO | 2016/078096 A1 | 6/2016 |

OTHER PUBLICATIONS

English Translation of Office Action dated Nov. 13, 2018 for CN application 201480081687.4.
Office action from JPO for JP application 2017513705, dated Apr. 23, 2018.
Smith D R, "Ligation-mediated PCR of restriction fragments from large DNA molecules" PCR Methods & Applications, Cold Spring Harbor Laboratory Press, Genome Res. 1992 2: 21-27.
Bennett E A et al, "Library construction for ancient genomics: single strand or double strand?", Biotechniques Rapid Dispatches, Informa Healthcare, US, vol. 56, No. 6, Jun. 1, 2014, pp. 289-290.
Gansauge, Marie-Theres et al, "Single-stranded DNA library preparation for the sequencing of ancient or damaged DNA", Nature Protocols, vol. 8, No. 4, Mar. 14, 2013, pp. 737-748.
Gansauge, Marie-Theres et al, "Single-stranded DNA library preparation from highly degraded DNA using T4 DNA ligase", Nucleic Acids Research, vol. 45, No. 10, Jan. 23, 2017.
Extended European Search Report issued for related application No. EP14901593.5, dated Jun. 13, 2017.
International Search Report issued for PCT/CN2014/091852, dated Jun. 9, 2015.
Written Opinion of the International Searching Authority issued for PCT/CN2014/091852, dated Jun. 9, 2015.
Ukai H., et al. "A new technique to prevent self-ligation of DNA" Journal of Biotechnology vol. 97, Dec. 31, 2002, pp. 233-242.
International Search Report issued for PCT/CN2014/086418, dated Jun. 15, 2015.
Written Opinion of the International Searching Authority issued for PCT/CN2014/086418, dated Jun. 15, 2015.
Office Action dated Mar. 14, 2019 for U.S. Appl. No. 15/510,890.
Final Office Action dated Mar. 14, 2019 for U.S. Appl. No. 15/510,890.

```
                        SEQUENCE LISTING

<160> NUMBER OF SEQ ID NOS: 5

<210> SEQ ID NO 1
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<223> OTHER INFORMATION: n is a, t, c or g
<220> FEATURE:
<221> NAME/KEY: misc_feature
<222> LOCATION: (12)..(12)
<223> OTHER INFORMATION: n is a, c, g, or t

<400> SEQUENCE: 1
gtcctaagac cngatcgggc ttcgactgga gactccgact t                    41

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide

<400> SEQUENCE: 2
agtcggaggc caagcggtct taggacat                                    28

<210> SEQ ID NO 3
<211> LENGTH: 41
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (11)..(20)
<223> OTHER INFORMATION: Tag sequence
<220> FEATURE:
<221> NAME/KEY: misc_feature
<222> LOCATION: (11)..(20)
<223> OTHER INFORMATION: n is a, t, c or g

<400> SEQUENCE: 3
agacaagctc nnnnnnnnnn gatcgggctt cgactggaga c                    41

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide

<400> SEQUENCE: 4
tcctaagacc gcttggcctc cgact                                       25

<210> SEQ ID NO 5
<211> LENGTH: 24
<212> TYPE: DNA
```

<210> ORGANISM: Artificial Sequence
<220> FEATURE:
<223> OTHER INFORMATION: Oligonucleotide

<400> SEQUENCE: 5
tcgagcttgt cttcctaaga ccgc                                    24

VESICULAR ADAPTOR AND USES THEREOF IN NUCLEIC ACID LIBRARY CONSTRUCTION AND SEQUENCING

CROSS-REFERENCE TO RELATED APPLICATIONS

This application is a U.S. continuation application of U.S. patent application Ser. No. 15/510,890 filed on Mar. 13, 2017, which is based upon PCT Application No. PCT/CN2014/091852 filed on Nov. 21, 2014, and claims a priority to and benefits of PCT Application No. PCT/CN2014/086418 filed with the National Intellectual Property Administration of PRC on Sep. 12, 2014, the entire contents of which are incorporated herein by reference.

FIELD

The present disclosure relates to the field of biotechnology, in particular, to a vesicular adaptor and a method for constructing a nucleic acid library and a method for sequencing the same.

BACKGROUND

The second-generation sequencing technology, also known as Next-generation sequencing technology, is named with respect to the first-generation sequencing technology which is represented by the Sanger sequencing method. The second-generation sequencing technology is represented by Roche/454 Pyrosequencing, Illumina/Solexa polymerase synthesis sequencing and ABI/SOLiD ligase sequencing, and their common characteristic is high sequencing throughput. Compared with these mainstream sequencing platforms, the Complete Genomics (CG) sequencing platform with the highest throughput may produce 9.9 TB of data in each run, and its output may reach 50 Gb per hour, which is 10-25 times that of the mainstream sequencing platforms. With respect to read length for haploidy, among the mainstream sequencing platforms, only the Illumina sequencer may achieve a read length of 8-10 kb for haploidy, while the CG sequencer may reach a read length greater than 99 kb. In addition, the CG sequencer may achieve accuracy up to 99.999%, better than other commercial sequencers. Thus, compared with the mainstream sequencing platforms, the CG sequencing platform has unique advantages.

In the process of constructing a nucleic acid sequencing library, it is generally necessary to introduce an adaptor with a known sequence for sequencing. However, it has been reported that when an adaptor is ligated for library construction in known way that not only ligating efficiency is not high enough, but also many by-products at low level arise. In addition, as the CG sequencing platform adopts a cyclic single-stranded library for sequencing, linear double-stranded libraries constructed for the mainstream sequencing platforms are thus not suitable for the CG sequencers. However, as to the method for constructing the cyclic single-stranded library for nucleic acid sequencing, there has been no literature reported so far.

Based on above situation, an adaptor with high ligating efficiency and accuracy is urgently required to be developed in the related art.

SUMMARY

The present disclosure provides a method for constructing a cyclic single-stranded library by use of an oligonucleotide vesicular adaptor, comprising:

(a) ligating the oligonucleotide vesicular adaptor with a double-stranded DNA fragment to provide a structure K1-K2-K3, wherein K2 represents the double-stranded DNA fragment, and K1 and K3 each represent an oligonucleotide vesicular adaptor ligated to K2 respectively at two terminals of K2;

(b) subjecting the double-stranded structure obtained in (a) to amplification under a pair of primers so as to obtain an amplified double-stranded DNA product;

(c) isolating a single-stranded DNA from the amplified double-stranded DNA product obtained in (b); and (d) subjecting the single-stranded DNA obtained in (c) to cyclization in the presence of a cycling single-stranded molecule, so as to obtain the cyclic single-stranded library, wherein the oligonucleotide vesicular adaptor comprises:

a 5' paired double-stranded region at a first terminal of the adaptor;

a 3' paired double-stranded region at a second terminal of the adaptor, comprising a first strand and a second strand complementary with each other, wherein the first strand of the 3' paired double-stranded region comprises an overhang at the 3' end thereof and the second strand of the 3' paired double-stranded region comprises a phosphorylated base at the 5' end thereof so as to provide a sticky terminal, and a vesicular non-paired region between the 5' paired double-stranded region and the 3' paired double-stranded region, wherein the vesicular non-paired region comprises a first strand and a second strand non-complementary with each other and the first strand of the vesicular non-paired region is of a length longer than that of the second strand of the vesicular non-paired region.

In an embodiment of the present disclosure, K1 and K3 are each ligated to K2 via the sticky terminal of the 3' paired double-stranded region.

In an embodiment of the present disclosure, the sticky terminal of the 3' paired double-stranded region of the oligonucleotide vesicular adaptor has a single base tail.

In an embodiment of the present disclosure, the single base tail is thymine (T).

In embodiments of the present disclosure, before the step (a), the method further comprises:

(e) end-repairing the double-stranded DNA fragment to obtain a double-stranded DNA fragment with blunt terminals; and (f) adding an adenine (A) base to each 3'-end of the double-stranded DNA fragment with the blunt terminals obtained in (e), to obtain a double-stranded DNA fragment with an A base at each 3' end thereof.

In embodiments of the present disclosure, the step (a) is performed by ligating the oligonucleotide vesicular adaptor to each terminal of the double-stranded DNA fragment with the A base at each 3'-end thereof obtained in (f) to obtain a double-stranded DNA fragment ligated with the oligonucleotide vesicular adaptor at each terminal thereof.

In embodiments of the present disclosure, in the step (b), one of the pair of primers is labeled with biotin.

In embodiments of the present disclosure, the step (c) is performed by isolating a single-stranded DNA labeled with biotin from the amplified double-stranded DNA product obtained in (b) by using beads coated with avidin through "avidin-biotin" combination, so as to obtain a single-stranded DNA without biotin for cyclization.

In embodiments of the present disclosure, after the step (d), the method further comprises:

(g) digesting uncyclized DNAs obtained in (d) with nucleases specifically digesting linear DNAs to obtain a pre-product; and (h) purifying the pre-product obtained in (g) to obtain the cyclic single-stranded library.

In embodiments of the present disclosure, the nucleases used in (g) comprise a first exonuclease specifically digesting linear single-stranded DNAs and a second exonuclease specifically digesting linear double-stranded DNAs.

In an embodiment of the present disclosure, the first strand of the vesicular non-paired region is longer than the second strand of the vesicular non-paired region by at least 5 to 30 nt.

In an embodiment of the present disclosure, the 5' paired double-stranded region also has a sticky terminal.

In an embodiment of the present disclosure, the 5' paired double-stranded region has a sticky terminal of 1 to 3 non-complementary bases.

In an embodiment of the present disclosure, the oligonucleotide vesicular adaptor comprises a sense strand and an antisense strand and is of a structure of formula I from the 5' terminal to the 3' terminal:

$$Y0-Y1-Y2 \qquad (I)$$

wherein

Y0 represents the 5' paired double-stranded region, and is of a length of 10-15 nt;

Y1 represents the vesicular non-paired region, the sense strand of the vesicular non-paired region being of a length 5-30 nt longer than that of the antisense strand of the vesicular non-paired region; and Y2 represents the 3' paired double-stranded region.

In an embodiment of the present disclosure, Y0 is of a length of lint.

In an embodiment of the present disclosure, the oligonucleotide vesicular adaptor is of a length of at least 20 nt.

In an embodiment of the present disclosure, the oligonucleotide vesicular adaptor is of a length of 25 to 50 nt.

In an embodiment of the present disclosure, the oligonucleotide vesicular adaptor is of a length of 30 to 45 nt.

In an embodiment of the present disclosure, the pair of primers comprises: a first primer having the same sequence as at least a portion of the first strand of the vesicular non-paired region; and a second primer, specifically pairing with the second strand of the vesicular non-paired region.

In an embodiment of the present disclosure, the avidin in (c) is streptavidin.

In an embodiment of the present disclosure, the pair of primers in (b) includes:

a forward primer:
5-/phos/AGACAAGCTCNNNNNNNNNN-GATCGGGCTTCGACTGGAGAC (SEQ ID NO.:3); and
a reverse primer: 5-/bio/TCCTAA-GACCGCTTGGCCTCCGACT (SEQ ID NO.:4), in which, 5-/phos/indicates that the 5' terminal nucleotide is modified by phosphorylation;

NNNNNNNNNN represents a tag sequence, where N represents adenine (A), thymine (T), cytosine (C) or guanine (G); and 5-/bio/indicates that the 5' terminal nucleotide is marked with biotin.

In an embodiment of the present disclosure, the cycling single-stranded molecule in (d) is of a sequence:

TCGAGCTTGTCTTCCTAAGACCGC.  (SEQ ID NO.: 5)

In an embodiment of the present disclosure, the nucleases include an enzyme mixture of Exo I and Exo III.

The invention enables provision of a method for constructing a cyclic single-stranded library for a high throughput sequencing platform that requires a cyclic single-stranded library, such as the Complete Genomics' sequencing platform.

DETAILED DESCRIPTION

The present inventors have for the first time developed a vesicular adaptor for efficiently constructing a nucleic acid sequencing library with high quality through extensive and in-depth studies and extensive screening. The experimental results show that, compared with sequencing data obtained from other nucleic acid sequencing library construction techniques, the nucleic acid sequencing library constructed with the vesicular adapter of the present disclosure has a higher quality and correlation, which can be used in the CG sequencing platform, thereby obtaining high authentic and reliable data without adverse influence on information analysis. Based on this, the present invention has been completed.

CG Sequencing Platform

For the CG sequencing platform, DNA nanoballs are embedded in a chip using high-density DNA nanochip technology, and bases in the sequence are read with combinatorial probe anchor ligation (cPAL) technology.

Cyclic single-stranded DNAs were obtained after library construction. A DNA nanoball (DNB), including more than 200 copies of cyclic single-stranded DNAs, was formed by rolling circle amplification, and then embedded into a hole in a chip using high-density DNA nanochip technology, with each hole only able to accommodate one DNA nanoball (as one DNA nanoball, once combined with the hole in the chip, will exclude the combination of other DNA nanoballs with the same hole). The occupancy rate of the DNA nanochip was over 90%, and each prepared DNA nanochip may accommodate 180 billion bases for imaging.

The cPAL technique uses probes marked with four different colors to read bases adjacent to the adaptor by at most 10 consecutive bases for each time. As each sequencing is independent from one another, i.e. the sequencing result is not affected by a previous sequencing result, thus error accumulation is avoided, which results in a high accuracy sequencing result with a base error rate as low as 1/100000. During sequencing, an anchor molecule is added to complementary pair with the adaptor, then the probes marked with four different colors are paired with corresponding bases of the template with the DNA ligases. The types of bases are determined by imaging fluorescent groups. Another advantage of cPAL technology is that, concentrations of probes and enzymes may be greatly reduced as the bases are read using a non-continuous and non-linkage combinatorial probe anchor ligation (cPAL) technology. Different from Sequencing by Synthesis, several bases may be read once in each cycle of cPAL, such that consumptions of sequencing reagents and imaging time may be both greatly reduced. Compared with the current popular next-generation sequencing technology, methods for constructing a library and sequencing the same according to embodiments of the present disclosure may obtain much more data while consuming fewer reagents.

Method for Constructing a Library

A RNA sample was digested with DNase I. The digested RNAs were purified with RNA clean magnetic beads. mRNAs from the total RNAs were isolated and purified with Oligo (dT) 25 magnetic beads, followed by fragmentation to obtain fragmented mRNAs. cDNAs were synthesized by reverse transcription of the fragmented mRNAs, and then end-repaired to form DNA fragments with blunt terminals to which were added A bases to obtain DNA fragments each with one A base at the 3'-terminal thereof. The obtained DNA fragments each with one A base at the 3'-terminal thereof were ligated with vesicular adaptors to obtain DNA fragments each ligated with the vesicular adaptor at each terminal thereof, which were purified with magnetic beads and then amplified through polymerase chain reaction (PCR) where one primer used is marked with biotin. PCR product thus obtained was isolated by magnetic beads coated with streptavidin to obtain PCR single-stranded product, which was cyclized by bridge oligonucleotides and T4 ligases. Uncyclized PCR single-stranded product was enzymatically digested to obtain the cyclic single-stranded library.

Cyclic Single-Stranded Library

The present disclosure also provides in embodiments a cyclic single-stranded library, which is suitable for sequencing and constructed by the above-described method for constructing a library.

In a preferred embodiment of the present disclosure, the present inventors have fully verified the stability, repeatability, and true reliability of the method of the present disclosure by exploring the optimum condition for constructing the library and comparing the results obtained under the optimum condition with that obtained by the other techniques. In addition, it is proved through several experiments with different samples that, the sequencing data obtained by the cyclic single-stranded library of the present disclosure is truly credible.

The advantages of the present disclosure lie in that:

(1) The vesicular adaptor for constructing the nucleic acid library is invented for the first time.

(2) With the use of a vesicular adaptor in embodiments of the present disclosure in the construction of the nucleic acid library, both the ligating efficiency and the efficiency of subsequent PCR are high and follow-up steps are few.

(3) The nucleic acid library in embodiments of the present disclosure may also be used in a sequencing platform which needs a cyclic single-stranded library.

(4) The method provided in embodiments the present disclosure is of high sequencing throughput, high accuracy and simple operation.

(5) The method provided in embodiments the present disclosure is of high stability, repeatability and reliability.

The present disclosure will be further described in the following with reference to specific embodiments. It should be appreciated that, these embodiments are merely used to illustrate the present disclosure and shall not be construed to limit the scope of the present disclosure. Experimental methods in the following embodiments, not specifying the detailed conditions, will be carried out according to conventional conditions, such as what is described in Sambrook et al., Molecular Cloning: Laboratory Manual (New York: Cold Spring Harbor Laboratory Press, 1989), or in accordance with conditions proposed by the manufacturer. Percentages and parts are by weight, unless otherwise stated.

Materials and Methods

In the following embodiments, the reagent was prepared as follows: 5× first strand buffer containing: 80-400 mM sodium chloride, 10-80 mM magnesium chloride, 200 mM to 300 mM Tris-HCl, phosphate, and water as solvent, with pH of 8.0-8.5. The standard substance, universal human reference RNA, was purchased from Agilent. Such RNA is a mixture from 10 kinds of human cell lines (breast cells, hepatoma carcinoma cells, cervical cells, embryonic cells, malignant glioma cells, melanoma cells, liposarcoma cells, lymphoma cells, leukemia T cells, and bone marrow B lymphocyte).

DNA fragments were purified by Ampure XP magnetic beads.

The materials used in embodiments of the present disclosure are all commercially available, unless specified otherwise.

Embodiment 1

Construction of RNA library with the use of the vesicular nucleotide adaptor

Figure 1:
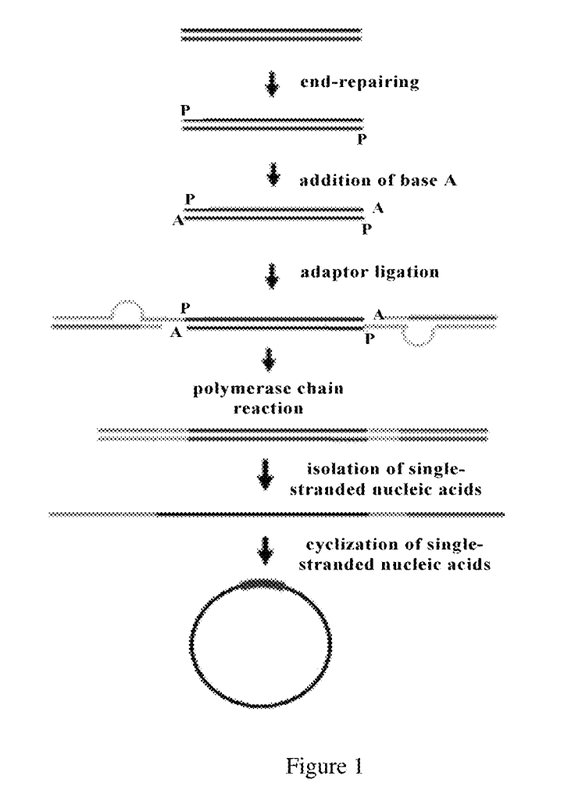
FIG. 1 is a flow chart showing the method for constructing a nucleic acid library according to an embodiment of the present disclosure.

The specific procedures were carried out as follows (see the procedures shown in FIG. 1):

The Specific Procedures:

1. mRNA Purification:

1) Standard, universal human reference RNA (3 Agilent), was added into an RNase-free tube and diluted into 50 μl with DEPC. The obtained mixture was denatured at 65° C. for 5 min subsequent to even mixing to degrade the secondary structure of RNA, then immediately placed on ice to obtain a RNA sample.

2) 15 μl Dynalbeads Oligo $(dT)_{25}$ magnetic beads were added into a non-stick-EP tube, washed twice with 100 μl binding buffer, then re-suspended in 50 μl binding buffer, followed by combining with the RNA sample obtained in 1), and finally stood still for 5 min at room temperature.

3) The non-stick-EP tube was placed on MPC (magnetic separator) for 2 min to remove the supernatant. The remaining magnetic beads were washed twice with 200 μl washing buffer. 50 μl binding buffer was added to a new non-stick-EP tube.

4) The EP tube (i.e. non-stick-EP tube in 3) containing magnetic beads was added with 50 μl 10 mM Tris-HCl and heated at 80° C. for 2 min to elute the mRNAs from the magnetic beads. Then the non-stick-EP tube was quickly transferred onto the MPC. The mRNAs were transferred into the new non-stick-EP tube containing the binding buffer in 3), the obtained mixture was denatured at 65° C. for 5 min to degrade the secondary structure of mRNAs, then immediately placed on ice. In addition, 200 μl washing buffer was immediately added into the tube containing the remaining magnetic beads to wash the magnetic beads twice.

5) 100 μl mRNA sample was added with magnetic beads washed twice and then stood still for 5 min at room temperature. The EP tube was placed on MPC for 2 min, the supernatant was carefully sucked out, and the remaining magnetic beads were washed twice with 200 µl washing buffer.

6) The EP tube containing magnetic beads was added with 17 µl 10 mM Tris-HCl, then heated at 80° C. for 2 min to elute mRNAs from the magnetic beads. The EP tube was quickly placed on MPC. The eluent containing mRNAs was transferred into a new 200 µl PCR tube. About 16 µl mRNA was recycled.

2. Fragmentation of mRNA and Synthesis of a First Strand

After combining with 3 µL 5× first strand buffer, the eluent obtained in the previous step was firstly incubated at 94° C. for 10 min followed by immediately placing on ice, then combined with 1 µl of random primers, and further incubated at 65° C. for 5 min to degrade the second structure followed by placing on ice. A reaction mixture, formulated with 100 mM DTT (2 µl), 25 mM dNTP mixture (0.4 µl) and RNase inhibitor (0.5 µl), was added into the tube containing RNA, followed by mixed to be uniform and then stood still for 2 min at room temperature, then combined with 1 µl Superscript II (200 U/µl) and water up to 25 PCR reaction was performed in accordance with the following procedures:

| Step 1 | 25° C. | 10 min |
|---|---|---|
| Step 2 | 42° C. | 50 min |
| Step 3 | 70° C. | 15 min |
| Step 4 | 4° C. | hold |

3. Synthesis of a Second Strand

After the above PCR reaction, the resulting reaction system was added to water up to 82.8 µl, then mixed with 10 µl 5× second strand buffer and 1.2 µl 25 mM dNTP mixture in sequence to be uniform, followed by placing on ice for 5 min, and then mixed with 1 µl RNaseH and 5 µl DNA Pol I to be uniform. Such obtained reaction system for synthesizing a second strand was incubated at 16° C. for 2.5 h.

After the reaction was completed, the resulting double-stranded product was purified with Ampure XP magnetic beads, and the purified double-stranded product (DNAs) was dissolved in 50 µl EB buffer.

4. End-Repairing

50 µl solution containing double-stranded DNAs obtained in the previous step was successively added with 27.4 µl water, 10 µl 10× end repair buffer, 1.6 µl 25 mM dNTP mixture, 5 µl T4 DNA polymases, 1 µl Klenow DNA polymases and 5 µl T4 PNK to form 100 µl reaction system which was incubated at 20° C. for 30 min.

After the reaction was completed, the end-repaired product was purified with Ampure XP magnetic beads and then dissolved in 32 µl EB buffer.

5. Base a Addition and Adaptor Ligation

32 µl solution containing end-repaired DNAs obtained in the previous step was successively added with 5 µl A-tailing buffer, 10 µl 1 mM dATP and 3 µl Klenow exo (inhibiting activities of exonucleases for digesting from 3'-end to 5'-end) to form a reaction system of 50 µl, which was incubated at 37° C. for 30 min.

After the reaction was completed, the base A-added product was purified with Ampure XP magnetic beads and then dissolved in 23 µl EB buffer.

Figure 2:
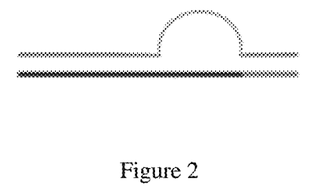
FIG. 2 is a diagram showing the structure of a vesicular adaptor according to an embodiment of the present disclosure.

23 µl solution containing base A-added product obtained in the previous step was successively added with 25 µl 2× Rapid T4 DNA Ligase Buffer, 1 µl vesicular adaptor (with a structure as shown in FIG. 2) mixture (containing the vesicular adaptor in an amount of 50 µmol) and 1 µl T4 DNA Ligase to form 50 µl reaction system, which was incubated at room temperature for 15 min.

The adaptor sequence was as follows:

```
                                    (SEQ ID NO.: 1)
5'-GTCCTAAGACCNGATCGGGCTTCGACTGGAGACTCCGACTT-3'

(SEQ ID NO.: 2)
5'-/phos/AGTCGGAGGCCAAGCGGTCTTAGGACAT-3'.
```

After the reaction was completed, the ligation product was purified with Ampure XP magnetic beads, and then dissolved in 10 µl EB buffer.

6. PCR Amplification and Purification

30 µl solution containing adaptor-ligated product obtained in previous step was successively added with 10 µl 5× Phusion butter, 1 µl PCR Primer F (5-/phos/AGACAAGCTCGATCGGGCTTCGACTGGAGAC)(SEQ ID NO.:3), 1 µl PCR Primer R (5-/bio/TCCTAA-GACCGCTTGGCCTCCGACT)(SEQ ID No.:4), 0.5 µl 25 mM dNTP mixture, 0.5 µl Phusion DNA polymases and 7 µl water to form 50 µl reaction system, which was incubated in the PCR instrument according to the following procedures:

a. 30 sec, 98° C.
b. 15 cycles:
  10 sec, 98° C.
  30 sec, 65° C.
  30 sec, 72° C.
c. 5 min, 72° C.
d. hold 4° C.

Figure 3:
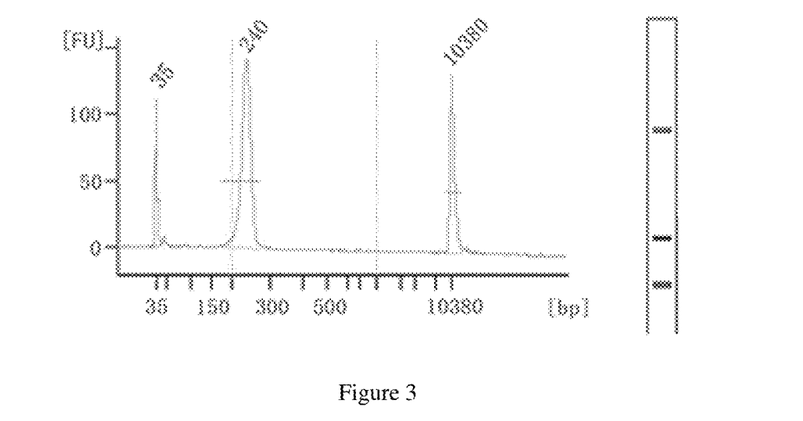
FIG. 3 is a diagram showing a result of a concentration of the purified PCR product detected by Agilent 2100 in nucleic acid library construction.

After the reaction was completed, the amplified PCR product was purified with Ampure XP magnetic beads and then dissolved in 32 µl EB buffer. The concentration of the purified PCR product was detected with Agilent 2100, and the results are shown in FIG. 3.

7. Isolation of a Single-Stranded Product 7.1 Washing magnetic beads coated with streptavidin 30 µl magnetic beads coated with streptavidin (for each sample) was mixed with 90 µl to 150 µl 1× magnetic beads binding buffer to be uniform in a non-stick tube, which was then placed on a magnetic separator for still standing and adsorption. The non-stick tube was adjusted to be in such a direction that enables the magnetic beads to move forward and backward in the 1× magnetic beads binding buffer, followed by discarding the supernatant. After the direction adjustment step was repeated once, the non-stick tube was taken out from the magnetic separator, an 30 µl 1× magnetic beads binding buffer added, followed by standing still at room temperature.

7.2 After combining with water up to 60 µl, the purified PCR product obtained in the step 6 was firstly mixed with 20 µl 4× magnetic beads binding buffer to be uniform, and then transferred into the non-stick tube obtained in 7.1 which contained magnetic beads dissolved in 30 µl 1× magnetic beads binding buffer, followed by mixing to be uniform. Such a resulting 110 µl mixture was incubated at room temperature for 15 to 20 min, during which the mixture was flicked gently once to make it distribute evenly.

7.3 The non-stick tube after the step 7.2 was placed on the magnetic separator for 3 to 5 min, followed by discarding the supernatant. The remaining magnetic beads were washed twice with 1 ml 1× magnetic beads washing buffer as described in step 7.1.

7.4 The magnetic beads after the step 7.3 were evenly mixed with 78 µl 0.1M NaOH by blowing up and down to obtain a mixture, followed by standing still for 10 min and then placed on the magnetic separator for 3 to 5 min. 74.5 µl supernatant thus obtained was transferred into a new 1.5 ml EP tube.

7.5 37.5 µl 0.3M MOPS was added into the 1.5 ml EP tube after the step 7.4, followed by mixed to be uniform, thereby obtaining 112 µl sample for use.

7.6 The 112 µl sample can be stored at −20° C.

8. Cyclization of the Single-Stranded Product 8.1 A primer reaction solution was formulated as follows about 5 min in advance:

(SEQ ID No.: 5)
ON1587 (TCGAGCTTGTCTTCCTAAGACCGC)

| | |
|---|---|
| water | 43 µl |
| 20 µM ON1587 | 20 µl |
| Total volume | 63 µl |

8.2 63 µl primer reaction solution obtained in the step 8.1 was mixed by shaking thoroughly, centrifuged, and then added into the sample of 112 µl obtained in step 7 (the starting amount n of the sample was critical and generally controlled within 100 ng≤n≤800 ng).

8.3 A ligase reaction solution was formulated as follows about 5 min in advance:

| | |
|---|---|
| water | 135.3 µl |
| 10 × TA Buffer (LK1) | 35 µl |
| 100 mM ATP | 3.5 µl |
| 600 U/µl Ligase | 1.2 µl |
| total | 175 µl |

8.4 175 µl ligase reaction solution obtained in step 8.3 was mixed by shaking thoroughly, centrifuged, and then added into the EP tube after step 8.2 which contained the primer reaction solution. A mixture thus obtained in this step was mixed by shaking for 10 s to be uniform, and then centrifuged.

8.5 The mixture obtained in step 8.4 was incubated in an incubator for 1.5 h at 37° C.

8.6 After the reaction was completed, 10 µl resulting sample was detected by electrophoresis detection a 6% denatured gel, and the remaining sample in about 350 µl was allowed to the next enzymatic reaction.

9. Enzyme Digestion 9.1 An enzyme-digesting reaction solution was formulated as follows about 5 min in advance:

| | |
|---|---|
| water | 1.5 µl |
| 10 × TA Buffer (LK1) | 3.7 µl |
| 20 U/µl Exo I | 11.1 µl |
| 200 U/µl Exo III | 3.7 µl |
| total | 20 µl |

9.2 20 µl enzyme-digesting reaction solution obtained in step 9.1 was mixed by shaking thoroughly, centrifuged, and then added into 350 µl sample obtained in the step 8.5 to obtain a mixture.

9.3 The mixture obtained in step 9.2 was mixed by shaking for 10 s to be uniform, and centrifuged, and then incubated in the incubator for 30 min at 37° C.

9.4 After 30 min, the enzymatic reaction was stopped by adding 15.4 µl 500 mM EDTA. 9.5 A sample obtained in step 9.4 was purified with 1.3× PEG32 magnetic beads/Tween 20 (or Ampure XP magnetic beads) as follows:

The sample obtained in step 9.4 was transferred into a 1.5 ml non-stick tube, and then combined with 500 µl PEG32 magnetic beads. The mixture thus obtained was left for binding at room temperature for 15 min, during which the mixture was mixed once by blowing up and down to be uniform.

9.6 The non-stick tube after step 9.5 was placed on the magnetic separator for 3 to 5 min, after which the supernatant was discarded, the remaining magnetic beads were washed twice with 700 µl 75% ethanol, during each of which the non-stick tube was reversed forward and backward to enable the magnetic beads to move 2 to 3 times in the ethanol.

9.7 The magnetic beads after washing were air dried, and then re-dissolved in 40 µl 1× TE for 15 min, during which the mixture thus obtained was mixed once to be uniform.

9.8 Supernatant from the mixture obtained in the step 9.8 was transferred into a new 1.5 ml EP tube, the final product was quantified with Qubit™ ssDNA Assay Kit.

Figure 4:
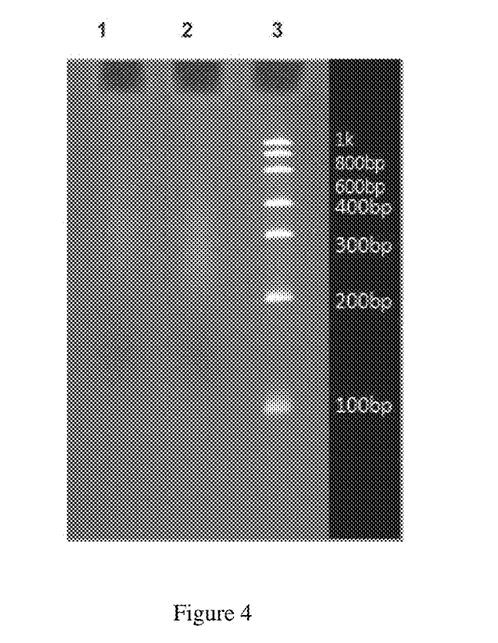
FIG. 4 is an electrophoretogram of libraries detected by a 6% TBE denatured gel, where lanes 1 and 2 each represent a cyclic single-stranded library, while lane 3 represents low range ssRNA ladder.

9.9 5 µl sample and 2 µl low Range RNA ladder were respectively mixed with 5 µl 2× RNA loading buffer to be uniform in different PCR tubes, both of which were incubated at 95° C. for 2 min for denaturation in a PCR instrument, and quickly cooled on ice for 5 min. The resulting samples were detected with a 6% TBE denatured gel. The results are shown in FIG. 4.

9.10 Concentration standardization

The initial amount of the sample prepared with DNA nanoball (DNB) was uniformly adjusted to 7.5 fmol/µl in accordance with the concentration at which the single-stranded molecules were quantitatively detected.

Embodiment 2

Comparison of PCR efficiency of the vesicular adaptor in the library construction with that of other types of adaptors The specific steps were as follows:

Steps same as those described in Embodiment 1 were carried out, where one adaptor was the vesicular adaptor, and the comparison adaptor was a matching adaptor. The PCR amplification and purification as described in step 6 were completed, after which the amount of purified PCR product was detected.

Concentration of PCR template and recycling concentration were measured with Qubit dsDNA Assay Kit.

The experimental result is shown in Table

| Adaptor | Matching adaptor | Vesicular adaptor |
|---|---|---|
| Amount of PCR template (ng) | 10 | 10 |
| Concentration of recycled product (ng/ul) | 5.66 | 53 |
| Total amount of recycled product (ng) | 226.4 | 2120 |
| PCR efficiency | 1.366 | 1.709 |

Note:
PCR efficiency = (total PCR yield/Initial amount of template) × (1/cycles)

It can be seen from above result that PCR efficiency of the vesicular adaptor is apparently higher than that of the matching adaptor.

All documents mentioned in the present disclosure are incorporated herein by reference, as if each document were individually recited for reference. Furthermore, it should be appreciated that, those skilled in the art can make various changes and modifications to the present disclosure based on the content described above, and those equivalents also fall into the scope defined by appended claims of the present disclosure.

What is claimed is:

1. A method for constructing a cyclic single-stranded library by use of an oligonucleotide vesicular adaptor, comprising:
   (a) ligating the oligonucleotide vesicular adaptor with a double-stranded DNA fragment to provide a structure K1-K2-K3, wherein K2 represents the double-stranded DNA fragment, and K1 and K3 each represent an oligonucleotide vesicular adaptor ligated to K2 respectively at two terminals of K2;
   (b) subjecting the double-stranded structure obtained in (a) to amplification under a pair of primers so as to obtain an amplified double-stranded DNA product;
   (c) isolating a single-stranded DNA from the amplified double-stranded DNA product obtained in (b); and
   (d) subjecting the single-stranded DNA obtained in (c) to cyclization in the presence of a cycling single-stranded molecule, so as to obtain the cyclic single-stranded library,
   wherein the oligonucleotide vesicular adaptor comprises:
   a 5' paired double-stranded region at a first terminal of the adaptor;
   a 3' paired double-stranded region at a second terminal of the adaptor, comprising a first strand and a second strand complementary with each other, wherein the first strand of the 3' paired double-stranded region comprises an overhang at the 3' end thereof and the second strand of the 3' paired double-stranded region comprises a phosphorylated base at the 5' end thereof so as to provide a sticky terminal, and
   a vesicular non-paired region between the 5' paired double-stranded region and the 3' paired double-stranded region,
   wherein the vesicular non-paired region comprises a first strand and a second strand non-complementary with each other and the first strand of the vesicular non-paired region is of a length longer than that of the second strand of the vesicular non-paired region.

2. The method according to claim 1, wherein K1 and K3 are each ligated to K2 via the sticky terminal of the 3' paired double-stranded region.

3. The method according to claim 2, wherein the sticky terminal of the 3' paired double-stranded region of the oligonucleotide vesicular adaptor has a single base tail.

4. The method according to claim 3, wherein the single base tail is thymine (T).

5. The method according to claim 1, wherein before the step (a), the method further comprises:
   (e) end-repairing the double-stranded DNA fragment to obtain a double-stranded DNA fragment with blunt terminals; and
   (f) adding an adenine (A) base to each 3'-end of the double-stranded DNA fragment with the blunt terminals obtained in (e), to obtain a double-stranded DNA fragment with an A base at each 3' end thereof.

6. The method according to claim 5, wherein the step (a) is performed by ligating the oligonucleotide vesicular adaptor as defined in claim 1 to each terminal of the double-stranded DNA fragment with the A base at each 3'-end thereof obtained in (f) to obtain a double-stranded DNA fragment ligated with the oligonucleotide vesicular adaptor at each terminal thereof.

7. The method according to claim 6, wherein in the step (b), one of the pair of primers is labeled with biotin.

8. The method according to claim 7, wherein the step (c) is performed by isolating a single-stranded DNA labeled with biotin from the amplified double-stranded DNA product obtained in (b) by using beads coated with avidin through "avidin-biotin" combination, so as to obtain a single-stranded DNA without biotin for cyclization.

9. The method according to claim 1, wherein after the step (d), the method further comprises:
   (g) digesting uncyclized DNAs obtained in (d) with nucleases specifically digesting linear DNAs to obtain a pre-product; and
   (h) purifying the pre-product obtained in (g) to obtain the cyclic single-stranded library.

10. The method according to claim 9, wherein the nucleases used in (g) comprise a first exonuclease specifically digesting linear single-stranded DNAs and a second exonuclease specifically digesting linear double-stranded DNAs.

11. The method according to claim 1, wherein the first strand of the vesicular non-paired region is longer than the second strand of the vesicular non-paired region by at least 5 to 30 nt.

12. The method according to claim 1, wherein the 5' paired double-stranded region also has a sticky terminal.

13. The method according to claim 1, wherein the 5' paired double-stranded region has a sticky terminal of 1 to 3 non-complementary bases.

14. The method according to claim 1, wherein the oligonucleotide vesicular adaptor comprises a sense strand and an antisense strand and is of a structure of formula I from the 5' terminal to the 3' terminal:

$$Y0\text{-}Y1\text{-}Y2 \tag{I}$$

wherein
Y0 represents the 5' paired double-stranded region, and is of a length of 10-15 nt;
Y1 represents the vesicular non-paired region, the sense strand of the vesicular non-paired region being of a length 5-30 nt longer than that of the antisense strand of the vesicular non-paired region; and
Y2 represents the 3' paired double-stranded region.

15. The method according to claim 14, wherein Y0 is of a length of 11nt.

16. The method according to claim 1, wherein the oligonucleotide vesicular adaptor is of a length of at least 20 nt.

17. The method according to claim 1, wherein the oligonucleotide vesicular adaptor is of a length of 25 to 50 nt.

18. The method according to claim 1, wherein the oligonucleotide vesicular adaptor is of a length of 30 to 45 nt.

19. The method according to claim 1, wherein the pair of primers comprises:

a first primer having the same sequence as at least a portion of the first strand of the vesicular non-paired region; and a second primer, specifically pairing with the second strand of the vesicular non-paired region.

\* \* \* \* \*